United States Patent
Bar et al.

(10) Patent No.: US 12,114,946 B2
(45) Date of Patent: Oct. 15, 2024

(54) TOOL GRIPPER WITH INTEGRATED CONCENTRIC SHUTTER AND METHODS FOR ITS USE

(71) Applicant: LEM Surgical AG, Bern (CH)

(72) Inventors: Yossi Bar, Bern (CH); Lior Kimron, Bern (CH); Gael Bornet, Bern (CH)

(73) Assignee: LEM Surgical AG, Bern (CH)

( * ) Notice: Subject to any disclaimer, the term of this patent is extended or adjusted under 35 U.S.C. 154(b) by 0 days.

(21) Appl. No.: 18/631,921

(22) Filed: Apr. 10, 2024

(65) Prior Publication Data

US 2024/0252265 A1  Aug. 1, 2024

Related U.S. Application Data

(63) Continuation-in-part of application No. PCT/IB2023/055047, filed on May 16, 2023.

(60) Provisional application No. 63/602,367, filed on Nov. 22, 2023, provisional application No. 63/342,363, filed on May 16, 2022.

(51) Int. Cl.
*A61B 34/30* (2016.01)
*A61B 34/00* (2016.01)

(52) U.S. Cl.
CPC ........ *A61B 34/30* (2016.02); *A61B 2034/305* (2016.02)

(58) Field of Classification Search
CPC .... A61M 2005/206; A61M 2005/3206; A61M 25/013; A61M 25/02; A61M 5/3204; A61M 5/3205; A61M 5/3287; A61M 5/3293; A61M 5/343
See application file for complete search history.

(56) References Cited

U.S. PATENT DOCUMENTS

| | | | |
|---|---|---|---|
| 9,125,680 B2 | 9/2015 | Kostrzewski et al. | |
| 10,716,958 B2 | 7/2020 | Neff | |
| 2009/0163929 A1 | 6/2009 | Yeung et al. | |
| 2018/0193101 A1 | 7/2018 | Hashimoto | |
| 2019/0336705 A1* | 11/2019 | Kopperschmidt .... | A61M 5/343 |

(Continued)

FOREIGN PATENT DOCUMENTS

| | | |
|---|---|---|
| JP | 2018030179 A | 3/2018 |
| WO | WO-2008101228 A2 | 8/2008 |

(Continued)

OTHER PUBLICATIONS

PCT/IB2023/055047 International Search Report and Written Opinion dated Sep. 25, 2023.

*Primary Examiner* — Scott Luan
(74) *Attorney, Agent, or Firm* — Wilson Sonsini Goodrich & Rosati

(57) ABSTRACT

A gripper for holding surgical tools is provided. The gripper incorporates a concentric and adjustable shutter mechanism that allows the gripper to hold tools of multiple different circumferences and tools that do not have perfectly circular circumferences. In the context of a centrally coordinated robotic system and, in particular, a surgical robotic system, the disclosed gripper allows the robotic system to deploy a large variety of surgical tools without regard to their circumference or precise circumferential dimensions. A robotic system using the disclosed gripper is able to deploy a wide variety of tools while always keeping the tools centered in the work area due to the concentric shutter design.

30 Claims, 4 Drawing Sheets

(56) References Cited

U.S. PATENT DOCUMENTS

| | | |
|---|---|---|
| 2021/0186615 A1 | 6/2021 | Shmayahu et al. |
| 2021/0338348 A1 | 11/2021 | Zehavi et al. |
| 2022/0079687 A1 | 3/2022 | Sexson et al. |
| 2022/0168048 A1 | 6/2022 | Shoham et al. |
| 2022/0241032 A1 | 8/2022 | Zucker et al. |
| 2022/0346882 A1 | 11/2022 | Zehavi et al. |

FOREIGN PATENT DOCUMENTS

| | | |
|---|---|---|
| WO | WO-2020061240 A1 | 3/2020 |
| WO | WO-2020069080 A1 | 4/2020 |
| WO | WO-2020079596 A1 | 4/2020 |
| WO | WO-2022044009 A1 | 3/2022 |
| WO | WO-2022195460 A1 | 9/2022 |
| WO | WO-2023067415 A1 | 4/2023 |
| WO | WO-2023118984 A1 | 6/2023 |
| WO | WO-2023118985 A1 | 6/2023 |
| WO | WO-2023144602 A1 | 8/2023 |
| WO | WO-2023223215 A1 | 11/2023 |
| WO | WO-2023237922 A1 | 12/2023 |

\* cited by examiner

TOOL GRIPPER WITH INTEGRATED CONCENTRIC SHUTTER AND METHODS FOR ITS USE

CROSS-REFERENCE TO RELATED APPLICATIONS

This application is a continuation-in-part of PCT Application No. PCT/IB2023/055047, filed May 16, 2023, which claims the benefit of U.S. Provisional No. 63/342,363, filed May 16, 2022; this application also claims the benefit of U.S. Provisional No. 63/602,367, filed Nov. 22, 2023, the contents of each of which are incorporated herein by reference in their entirety.

BACKGROUND

Field

The disclosed technology relates generally to medical apparatus and methods. More particularly, the disclosed technology relates to surgical robots and surgical robotic tools and to methods and systems for robotically manipulating surgical robotic tools.

Robotic surgery and surgical robots are now in common use. A typical robotic surgical procedure requires deploying one or more surgical tools and end effectors on multiple surgical robotic arms using one or more robotically controlled cameras/sensors that may be located at varying distances and angulations from the surgical field. Accurate and precise placement of each of the tools and end effectors is necessary for the safe and successful completion of such robotic surgical procedures.

Positioning of the surgical tools and end effectors is often achieved "kinematically" where the surgical robot controls and tracks each tool and end effector based on the dimensions and angulations of each segment of a robotic arm in the robotic coordinate space. While kinematic tracking of the robotic arms can be very accurate, tracking of the tools themselves depends on accurately knowing the dimensions of the tool as well as the details of how the tool is attached to the robotic arm which can be difficult. Accounting for the dimensions and orientation of the tool in the surgical robotic coordinate space is even more challenging when the tool or other surgical object is held in a gripper.

Grippers are used in wide variety of surgical and other robotic fields to hold and manipulate tools or other objects which cannot themselves be directly attached to a robot arm. Typically, a gripper is mounted at the distal end of a robotic arm and can be controlled to accommodate tools having a variety of different shapes and dimensions. It is important that the gripper be able to hold teach tool a known and precise orientation relative to the surgical robotic arm to allow the surgical system to kinematically position and operate the tool in a surgical procedure.

Grippers are of particular use in holding and manipulating elongate surgical tools, such as cannulated instruments in bronchial, urological, gynecological, orthopedic, and other procedures; endoscopic tools in bronchoscopic, laparoscopic, thoracoscopic, and other minimally invasive procedures; and catheters in vascular and neurovascular procedures. Such tools are often not designed for use in surgical robotic procedures and lack any interface or structure for direct attachment to a surgical robotic arm. In many instances, it will be desirable to use tools from different manufactures where some or all the tools will be intended for conventional (not robotic) surgeries.

Thus, there is a need for robotic surgical systems that can deploy a variety of elongate and other surgical tools including tools not designed to be manipulated by a robot and surgical tools having a range of sizes and shapes. In particular, it would be desirable to provide alternative and improved surgical robotic tool grippers that can accommodate a wide variety of surgical tools while holding each tool in a known and fixed orientation relative to a supporting robotic arm. It would be further desirable if such grippers were to be able to hold elongate tools along a known and precise center line, often transverse to the distal segment of the supporting robotic arm, regardless of the tool's width, diameter, cross-sectional shape, or other specifications. Other desirable features include providing circular peripheral gripping surfaces with variable diameters that can hold tools, probes, and assemblies having both circular and non-circular outer surfaces. Such circular gripping surfaces allow the grip tightness to be finely adjusted. At least some of these objectives will be met by the technologies disclosed herein.

Background Art

Surgical robotic tool grippers are described in US2009/163929 and US2019/0336705. WO2020/069080, WO2020/061240, WO2020/0079596, and WO2008/101228 describe surgical robots configured to manipulate elongated surgical tools. Relevant commonly owned publications and applications include PCT application no. PCT/IB2022/052297 (published as WO2022/195460); PCT application no. PCT/IB2022/058986 (published as WO2023/067415); PCT application no. PCT/IB2022/058972 (WO2023/118984); PCT application no. PCT/IB2022/058982 (WO2023/118985); PCT application no. PCT/IB2022/058978 (published as WO2023/144602); PCT application no. PCT/IB2022/058980 (published as WO2023/152561); PCT application no. PCT/IB2023/055047 (published as WO2023/223215); PCT application no. PCT/IB2022/058988 (published as WO2023/237922), the full disclosures of each of which are incorporated herein by reference.

SUMMARY

Grippers constructed in accordance with the disclosed technologies will typically be able to hold a random tool with random diameter and/or with a non-perfect circular shape, but no matter the tool's diameter, the gripped tool's center can always be in the same location which is known to the robot controller. In this regard, the robot can hold any random tool and regardless of its different diameter a center of the tool's point of attachment can always be in the same place which is known to the robotic controller. This is essential to the robotic system's ability to perform procedures accurately—if the robot does not know where the center of the robotic tool is, it cannot accurately guide the tool to the location of interest, or in the case of robotic surgery, to the anatomy of interest. This use case is best served by a gripper that can hold a tool concentrically, with a "shutter" being an excellent mechanism for accomplishing this goal. Moreover, a standard gripper may hold and firmly grip the tool, while this disclosed technology describes a gripper/shutter mechanism that allows to close the shutter around the tool and then open the shutter in the exact required amount to facilitate the required margins for a certain amount of motion of the tool inside the shutter. A gripper incorporating a concentric shutter is not available in medical robotics, in robotics generally, or in any field for that matter.

As used herein, the term "shutter" refers to any mechanical closure device that has a variable aperture for grasping a tool or other surgical object that is to be held and manipulated by the tool gripper. Exemplary shutters can comprise a pair of opposed bodies that can positioned or adjusted in some way to open and close about a tool or other object positioned therebetween. The opposed bodies can be rotatable (configured to rotate about their respective axes) to orient tapered grooves on their outer surfaces to form a gripping surface with a generally continuous circular periphery with (1) a diameter that depends on the rotational positions of the opposed bodies and (2) a center that remains fixed relative to the gripper mechanism regardless of the rotational positions of the opposed bodies.

Exemplary grippers in accordance with the disclosed technologies often comprise an integrated concentric shutter mechanism for grasping an essentially unlimited range of tools and cannulas with varying random diameters. Exemplary grippers incorporate a "shutter" mechanism that centers a tool in the gripper regardless of the tool's diameter or precise dimensions. For elongate tools and cannulas having shafts with circular cross-sections, the shutter mechanisms can accommodate tools having shafts with non-circular peripheries, including oval, polygonal, rectangular, and other regular and irregular circumferences.

Centering of the tool is essential to the tool being deployed and operated accurately. This is particularly true of a tool deployed by a robotic system, or in a specific example, by a surgical robotic system, where the grasper is being positioned with reference at least partially to the kinematics of the robotic arms. In such robotic systems, a central control unit controls the positions of the robotic arms to deploy a working end of the tool toward a target location or anatomy. Accurate positioning of the working end can only be achieved if the tool is reliably and concentrically centered in the gripper. In that way, the tool can be targeted accurately based on the robotic system knowing the location of the end effector relative to the known location of the center of the tool.

Optionally, the grippers disclosed herein may also be configured to open and close in a jaw-like fashion to allow placement over a middle portion of an elongate tool without having to pass or "thread" a length of the tool between shutters that cannot be spread open to allow access.

The gripper with integrated concentric shutter mechanism of the present disclosed technology has several inherent advantages over the current state of the art, which does not provide an integrated device that can center a wide variety of tools concentrically. Namely, the disclosed device may open and close like a conventional gripper—in other words, it can open and close its "jaws" to hold and release a wide variety of longitudinal tools around their circumference. For the disclosed gripper to hold tools in this manner, the tools do not need to have perfectly circumferential dimensions, but the term "circumference" is used for ease of understanding. Another key advantage is that the disclosed device has a shutter mechanism. Thus, a tool or instrument can always be concentrically centered in an end effector and, in this way, a robotic system can always know where the center of a gripped tool is, regardless of the precise identity, design or dimensions of the tool. Also advantageously, the integrated shutter mechanism creates a perfect circle around the gripped tool, even if the tool's dimensions are not perfectly circumferential. Accordingly, the tool can be rotated about its own longitudinal axis which may be important for many applications, including robotic surgical applications. The presently available gripper, however, has a smooth and consistent circumferential surface in contact with the tool that allows for easy motorized rotation. Finally, the ability to add to the basic shutter design, also the additional gripper design ("jaws" that open and close), the disclosed device is relatively simple in external design and may thus be cleaned and sterilized easily—a key feature for end effector compatibility in the surgical robotics context.

In some instances, the disclosed grippers having integrated, concentric shutter mechanisms may include three main parts. A compartment houses the electronic parts, such as a motor and controller. In the context of a robotic surgical application, this compartment would be non-sterile and will be covered by a sterile cover. Needless to mention that this compartment can of course be designed to be completely sealed and by that being sterilized but this would result in more costly design and manufacturing. The suggested design offers a simple and cost-effective unit. Next, a shaft for motion transfer from the motor to the gripper is provided. The shaft would typically be sterile in the robotic surgery context (e.g. autoclave sterile). Finally, the gripper unit itself is provided and would of course be sterile in the robotic surgical context. The concentric shutter incorporated into the gripper unit comprises two opposing pairs of curved cylinders that, when deployed in combination, create a circular engagement point for grasping tools of varying diameters and dimensions.

Examples of integrated concentric shutter mechanisms include one or more one pairs of opposed cylindrical, spherical, or other bodies where at least a portion of each body has a cylindrical peripheral surface with a circumferentially oriented tapered groove formed therein. The cylindrical surface will typically extend over at least 120°, usually at least 180°, often at least 270°, and sometimes a full 360°, of the opposed body surface.

The tapered grooves are shaped similarly and have partial circular cross-sections with radii that decrease from an initial end of the groove to a terminal end of the groove. The opposed bodies are typically configured to counterrotate about their respective axes to orient the tapered grooves to form a gripping surface with a generally continuous circular periphery having a diameter that will vary as the opposed bodies are counterrotated. In other less preferred instances, the orientation of the tapered groves on one of the opposed bodies could be reversed which would allow the opposed bodies to be rotated in the same direction to open and close the aperture. Such unidirectional rotation, however, could have a tendency to torque the tool or other object being held by the gripper so is less preferred.

In a still further aspect, the present disclosed technology provides a method for robotically or otherwise manipulating a surgical tool. The method utilizes a gripper mechanism including integrated concentric shutter mechanisms attached to an arm of a surgical robot, as previously described. The concentric shutter mechanisms are initially opened to provide a passage therebetween, and a shaft or other component of an elongate surgical tool, cannula or the like is then advanced through the passage, and the concentric shutter mechanisms are then closed to center and frictionally engage the tool.

In some embodiments, the concentric shutter mechanisms comprise a pair of opposed bodies carried by the gripper mechanism, as described above. Closing the concentric shutter mechanisms comprises rotating the opposed bodies to frictionally engage the elongate tool in the tapered grooves, where the amount of friction is controlled by the degree of rotation of the opposed bodies.

In some instances, the concentric shutter mechanisms are mounted on a pair of jaws on the gripper, where the jaws are opened to is opened to create a larger space between concentric shutter mechanisms. An elongate surgical tool maybe placed between said opened jaws, and the jaws are closed to capture the elongate tool between the pair of opposed bodies with one body carried by each jaw.

In some embodiments, each opposed body has a circular peripheral surface with a circumferentially oriented tapered groove formed therein, said grooves forming a variable diameter aperture therebetween. The diameter can be finely adjusted simply by rotating the opposed bodies, where rotation can be accomplished by a single stepper or other positionable motor coupled to the opposed bodies by a single shaft and a simple gear mechanism.

In such instances, rotating the opposed bodies typically comprises counterrotating the opposed bodies to vary a diameter of the aperture.

In some instances, the diameter of the aperture in the gripper mechanism is varied to match a circumference of the tool being held by the gripper mechanism.

In some instances, the diameter of the aperture in the gripper mechanism is varied to adjust a holding friction between the opposed bodies and the elongate tool.

In some instances, the methods of the present disclosed technology further comprise adjusting the friction to allow the elongate tool to be rotated, advanced, and/or retracted relative to the gripper while still being held by the gripper.

In some instances, the methods of the present disclosed technology, further comprise at least one of rotating and axially translating the elongate tool while said elongate tool is being held by the gripper.

In some instances, the elongate tool is circumferentially centered in the gripper mechanism.

In some instances, the elongate tool has a circular periphery held by the gripping mechanism.

In some instances, the elongate tool has a non-circular periphery held by the gripper mechanism but is still circumferentially centered in the gripper mechanism.

In some instances, methods of the present disclosed technology further comprise selectively attaching and detaching the gripper mechanism to a motor.

In some instances, methods of the present disclosed technology further comprise performing a surgical procedure with the tool while held by the gripper mechanism.

In some instances, the gripper mechanism is positioned in a non-sterile field during the surgical procedure.

In some instances, methods of the present disclosed technology further comprise sterilizing the gripper mechanism after performing the surgical procedure.

In yet another aspect, the disclosed technology provides a gripper assembly for holding tools comprising a housing configured for mounting on a robotic arm. The gripper assembly comprises a gripper mechanism coupled to the housing where the gripper mechanism includes at least one pair of opposed bodies each having a cylindrical or other curved peripheral surface. The cylindrical peripheral surfaces are configured to define opposed, arcuate gripping surface which together define a generally circular periphery with (1) a diameter that depends on the rotational positions of the opposed bodies and (2) a center that remains fixed relative to the gripper mechanism regardless of the rotational positions of the opposed bodies.

In some instances, the cylindrical peripheral surfaces have circumferentially oriented tapered grooves formed therein, the tapered grooves are shaped similarly and have radii that decrease from an initial end of the groove to a terminal end of the groove and wherein the opposed bodies are configured to rotate about their respective axes to orient the tapered grooves to form the generally circular periphery.

In some instances, the gripper assembly further comprises a shaft having a distal end connected to the gripper mechanism and a proximal end configured to be connected to a motor which can rotate the shaft to counterrotate the opposed bodies.

In some instances, the gripper assembly further comprising a gear chain configured to transfer rotation from the shaft to the opposed bodies.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

With reference now to the figures and several representative embodiments, the following detailed description is provided.

Figure 1:
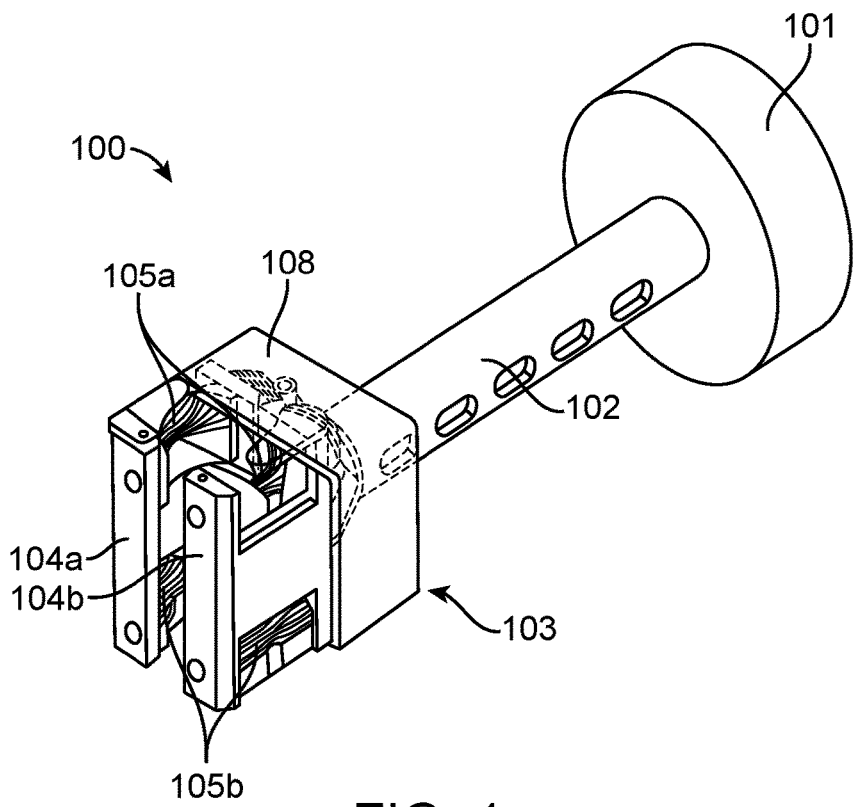
FIG. 1 is an isometric view of a tool gripper with integrated concentric shutter constructed, in accordance with some embodiments.
Figure 2:
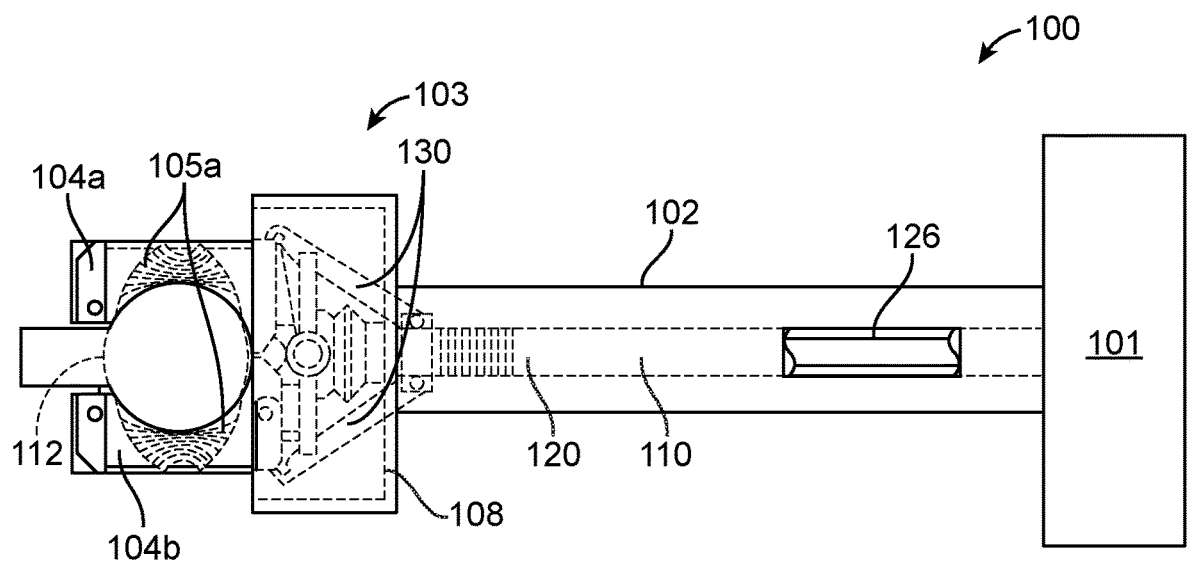
FIG. 2 is a top plan view of the tool gripper with integrated concentric shutter of FIG. 1, in accordance with some embodiments.

In some embodiments as shown in FIGS. 1 and 2, a tool gripper 100 with an integrated concentric shutter assembly may include three components. A non-sterile compartment 101 may house electronic parts, such as a motor and a controller. The non-sterile compartment 101 can typically be designed to sit outside the sterile field during surgery and can typically be configured to be detachable from components the device which are intended to be placed within the sterile field.

A sterile shaft housing 102 may be detachably secured to the non-sterile compartment 101 and carry a drive shaft 110 designed to transfer motion form the motor of the non-sterile compartment to a gripper 103 attached to a distal end of the shaft housing. The gripper 103 comprises jaws 104a and 104b which are configured to open and close like a standard gripper or grasper. The gripper 103 further comprises two opposing pairs of concentric rotatable bodies, also referred to as "shutters," 105a and 105b which may be rotated to adjust the diameter of a circular aperture 112 to accommodate tools of varying widths or diameters. The gripper components can be located in or mechanically coupled to a gripper housing 108.

While the tool gripper 100 can include jaws 104a and 104b to perform an initial grasp of a surgical tool, that capability is not essential, and embodiments described herein may rely on the concentric shutters alone to open an aperture sufficiently large to accommodate loading of a tool therebetween.

Figure 3A:
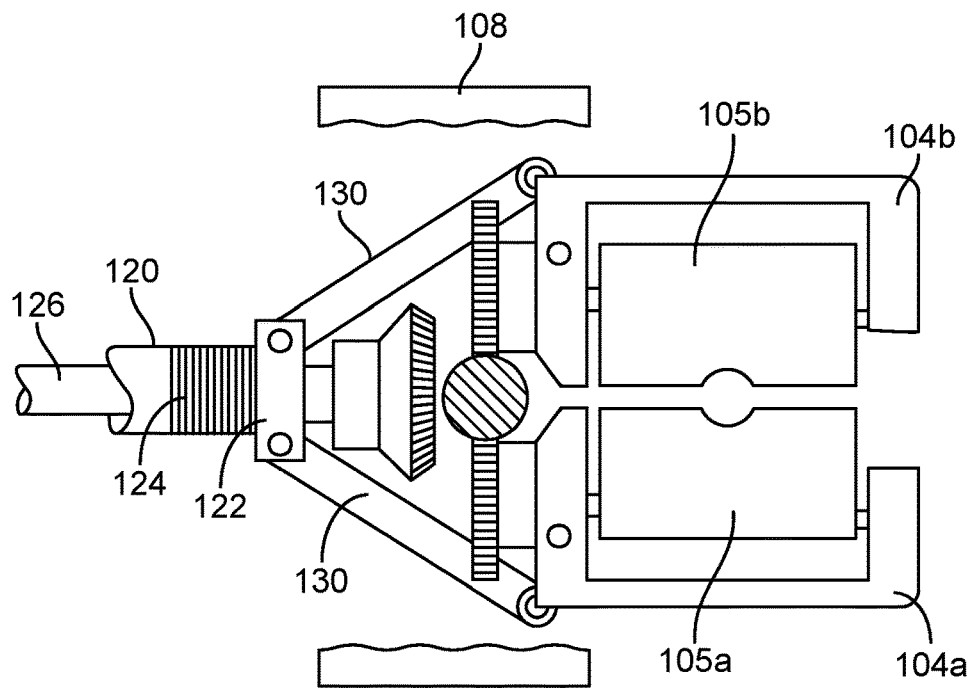
FIGS. 3A and 3B are top schematic views of the gripper of FIGS. 1 and 2 shown with gripper jaws in their closed and opened configurations, respectively, in accordance with some embodiments.
Figure 3B:
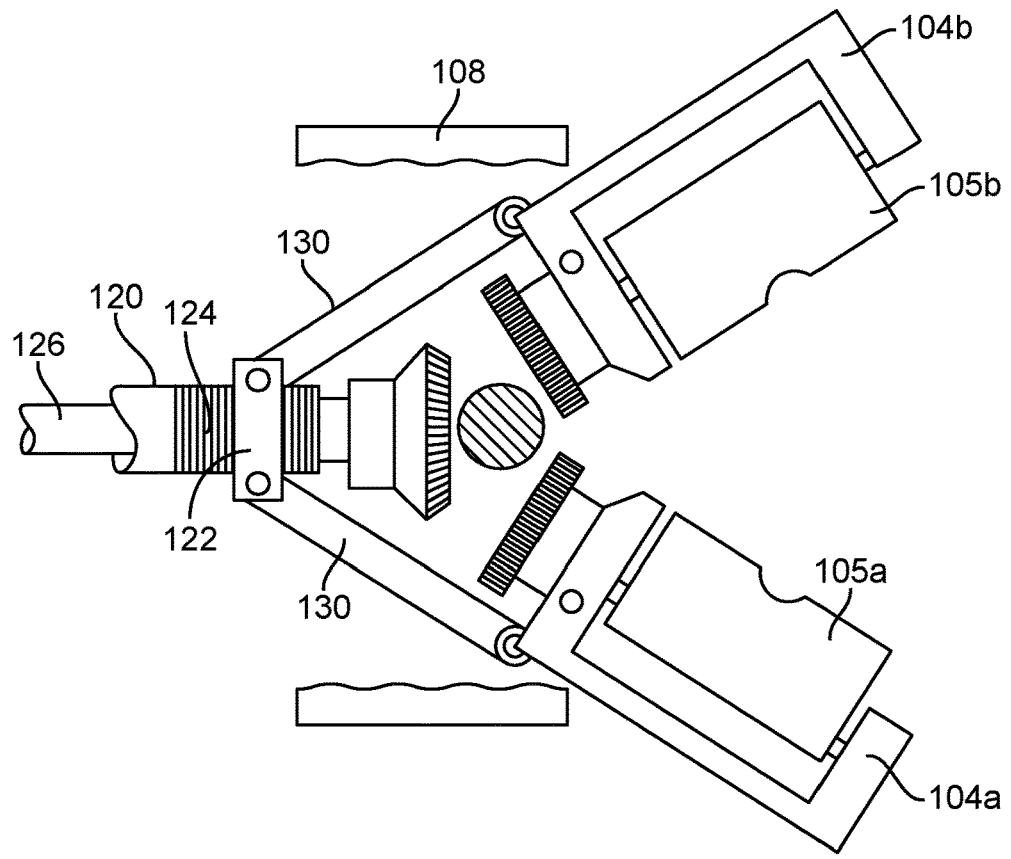

Referring now to FIGS. 3A and 3B, the gripper jaws 104a and 104b are opened and closed by rotation of an outer sleeve 120 of the drive shaft 110. A follower 122 can be mounted on a threaded distal region 124 of the outer sleeve 120 and axially translate in response to rotation of the outer sleeve. The direction of translation of the follower can depend on the direction of rotation, of the outer sleeve. The follower 122 can be linked to the jaws 104a and 104b by levers 130 which are pivotally attached at each end to the follower and the jaws, respectively. The jaws 104a and 104b can be pivotally attached to the gripper housing so that rotation of the outer sleeve 120 in a first direction causes the follower to move proximally which opens the jaws, as seen in FIG. 3B. Rotation of the outer sleeve 120 in the opposite direction can close the jaws 104a and 104b.

Figure 4A:
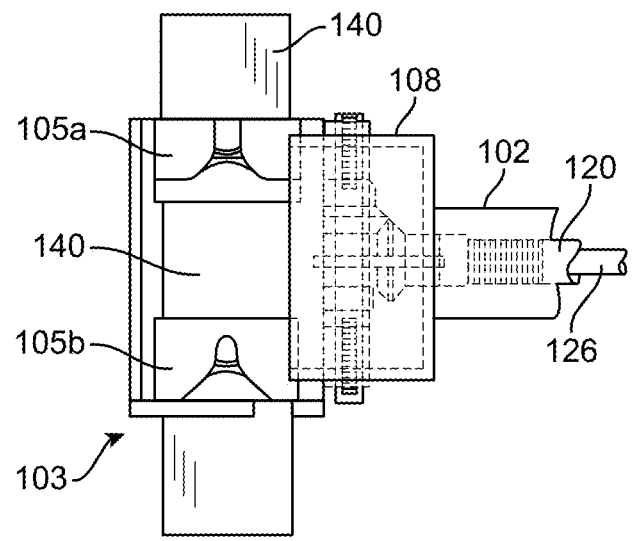
FIGS. 4A and 4B are side and top views of the gripper of FIGS. 1 and 2 shown holding a large diameter surgical tool, in accordance with some embodiments.
Figure 4B:
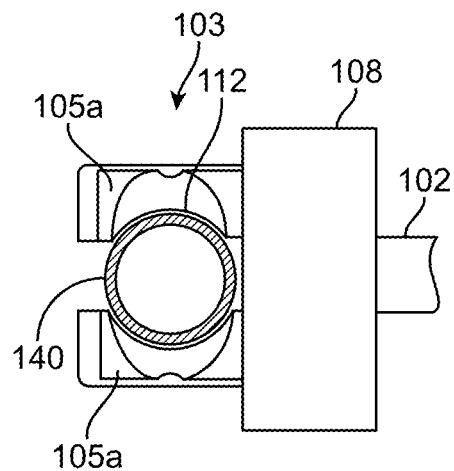

Referring now to FIGS. 4A and 4B, a large diameter tool, such as a cannula 140, can be grasped by the gripper 103 by rotating the opposed bodies 105a and 105b to open the aperture 112 to a size sufficient to accommodate the tool diameter. Optionally, this is done before or while the jaws 104a and 104b are opened as just described with reference to FIGS. 3A and 3B. Alternatively, it may not be necessary to open the jaws 104a and 104b (or the gripper may not have openable jaws as described with reference to FIG. 7 below), and the opposed bodies 105a and 105b may be rotated to allow passage of a tool therebetween without opening the jaws. In both cases, once the tool has been introduced, the opposed bodies can be rotated to reduce the aperture diameter 112 to grip the cannula 140 more firmly. The disclosed technology is particularly advantageous as it allows the user to finely adjust the rotation of the opposed bodies 105a and 105b to provide a desired tightness of grip, e.g., allowing a user to manually adjust the position of the cannula 140 while the cannula remains constrained by the gripper 103.

Figure 5A:
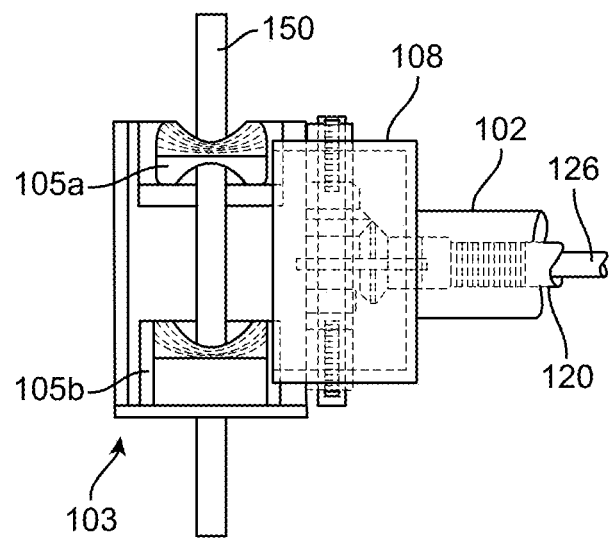
FIGS. 5A and 5B are side and top views of the gripper of FIGS. 1 and 2 shown holding a small diameter surgical tool, in accordance with some embodiments.
Figure 5B:
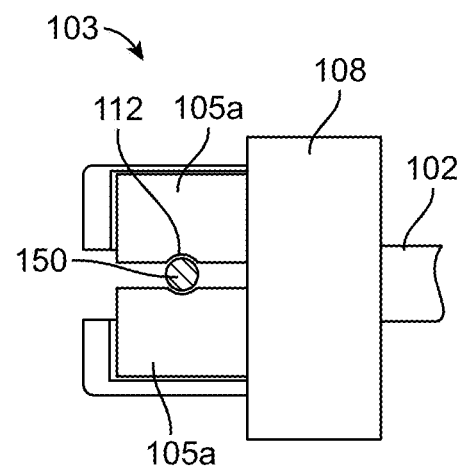

Referring now to FIGS. 5A and 5B, a small diameter tool, such as a probe 150, can be grasped by the gripper 103 where the opposed bodies 105a and 105b are rotated to provide a small diameter aperture 112. All other steps are generally as described with reference to FIGS. 4A and 4B.

Figure 6:
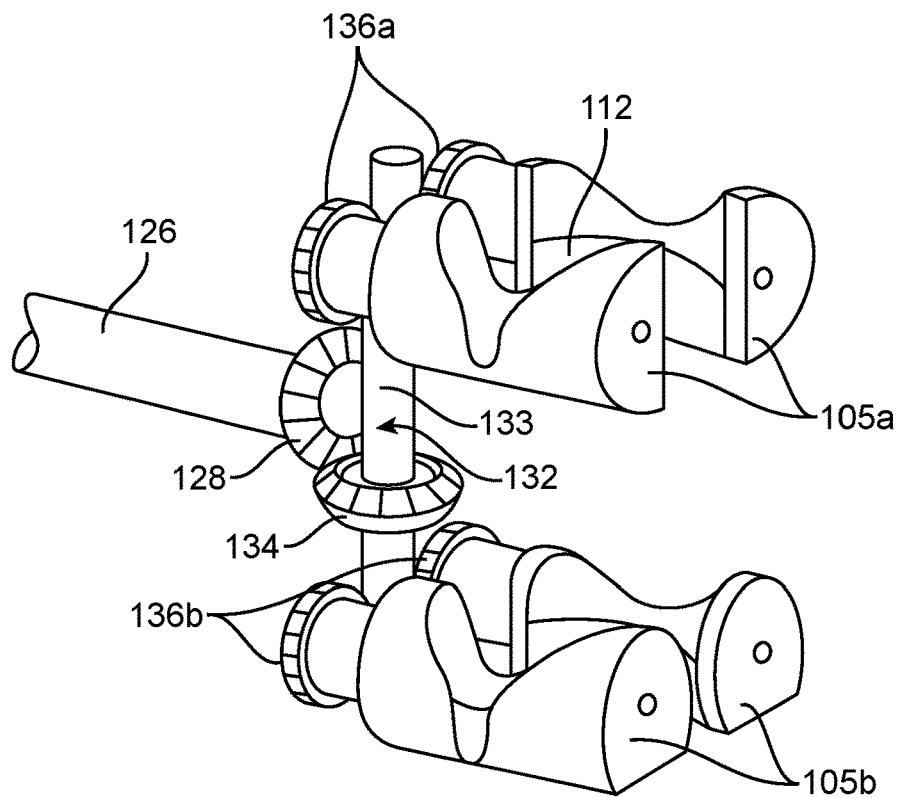
FIG. 6 is an isolated view of an exemplary gear chain for rotating the shutters of the gripper of FIGS. 1 and 2, in accordance with some embodiments.

Rotation of the opposed bodies 105a and 105b to adjust the aperture 112 diameter can be effected by the exemplary gear chain illustrated in FIG. 6. A motor (not illustrated), typically a stepper motor disposed in the non-sterile compartment 101 (FIG. 1), can rotate the rotating rod 126 which is coaxially disposed in the outer sleeve 120 of shaft housing 102 (FIG. 2). A primary drive gear 128 at a distal end of the rotating rod 126 can engage a worm drive gear 134 to rotate worm gear 132. The worm gear 132 can comprise a vertical shaft 133 having upper and lower spiral gear surfaces (best seen in FIG. 7), which engage and drive secondary drive gears 136a and 136b to rotate the opposed bodies 105a and 105b. Thus, the aperture 112 can be opened by rotating the rod 126 in a first direction and be closed by rotating the rod in the opposite direction.

Figure 7:
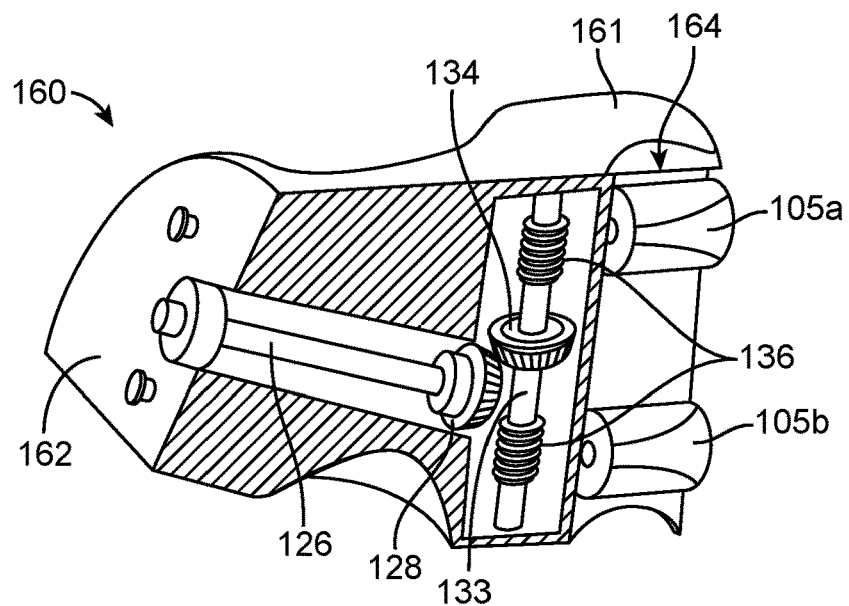
FIG. 7 is a sectional view of a gripper having stationary jaws constructed, in accordance with some embodiments.

Referring now to FIG. 7, a tool gripper 160 having stationary jaws 161 is illustrated. The tool gripper 160 can comprise a gripper body 162 which defines a fixed-diameter tool receiving passage 164 in which the opposed bodies 105a and 105b are located. The gear chain for rotating the opposed bodies 105a and 105b to adjust the aperture 112 diameter can be identical or similar to that described in FIG. 6, and the primary difference with the gripper embodiments described earlier is that the jaws do not open.

One of skill in the art will understand that only one modality for translating the energy generated by the motor to the jaws of the gripper has been described and that other equivalent and non-equivalent designs may exist. The gripper element itself can house a vertical shaft that can engage in rotational motion from energy also provided by the motor in the non-sterile compartment. The rotational motion of this horizontal shaft in turn can engage gears that, in turn, rotate the pairs of concentric shutter elements inward or outward to make the concentric opening in the gripper mechanism larger or smaller to accommodate tools of different sizes, Reference numbers used herein are listed in TABLE 1 below.

TABLE 1

| | |
|---|---|
| 100 | Tool gripper |
| 101 | Non-sterile compartment |
| 102 | Sterile shaft housing |
| 102a | Drive shaft |
| 103 | Gripper |
| 104a/b | Jaws |
| 105a/b | Opposed bodies (shutters) |
| 108 | Gripper housing |
| 109 | Drive shaft |
| 112 | Circular aperture |
| 120 | Outer sleeve |
| 122 | Follower |
| 124 | Threaded distal region |
| 126 | Rotating rod |
| 128 | Primary drive gear |
| 130 | Levers |
| 132 | Worm gear |
| 133 | Vertical shaft |
| 134 | Worm drive gear |
| 136 | Spiral gear surfaces |
| 136a/b | Secondary drive gears |
| 140 | Cannula |
| 150 | Probe |
| 160 | Tool gripper with stationary jaws |

TABLE 1-continued

| 162 | Gripper body |
| 164 | Tool-receiving passage |

Clause 1: A gripper assembly for holding tools, said gripper assembly comprising:
a housing configured for mounting on a robotic arm;
a gripper mechanism coupled to the housing and comprising at least one pair of opposed bodies each having a cylindrical peripheral surface with a circumferentially oriented tapered groove formed therein;
wherein the tapered grooves are shaped similarly and have partial circular cross-sections with radii that decrease from an initial end of the groove to a terminal end of the groove and wherein the opposed bodies are configured to rotate about their respective axes to orient the tapered grooves to form a gripping surface with a generally continuous circular periphery with (1) a diameter that depends on the rotational positions of the opposed bodies and (2) a center that remains fixed relative to the gripper mechanism regardless of the rotational positions of the opposed bodies.

Clause 2: The gripper assembly of Clause 1, wherein the opposed bodies are configured to counterrotate.

Clause 3: The gripper assembly of Clause 1, further comprising a shaft having a distal end connected to the gripper mechanism and a proximal end configured to be connected to a motor which can rotate the shaft to counterrotate the opposed bodies.

Clause 4: The gripper assembly of Clause 3, further comprising a gear chain configured to transfer rotation from the shaft to the opposed bodies.

Clause 5: The gripper assembly of Clause 4, wherein the gear chain includes a vertical shaft having a worm gear which drives gear wheels connected to each of the opposed bodies.

Clause 6: The gripper assembly of Clause 3, wherein the gripper mechanism further comprises a pair of jaws pivotally attached to the housing, Clause 7: The gripper assembly of Clause 6, wherein each jaw carries one of the opposed bodies of each pair.

Clause 8: The gripper assembly of Clause 7, wherein the jaws are configured to move the tapered grooves on the opposed bodies into and out of proximity to facilitate positioning tools therebetween.

Clause 9: The gripper assembly of Clause 8, further comprising a lever assembly coupled to the shaft and configured to transfer axial translation of the shaft to open and close the jaws.

Clause 10: The gripper assembly of Clause 1, wherein the opposed bodies are configured to control an amount of friction applied to a tool held by the opposed bodies in response to a degree of rotation of the opposed bodies.

Clause 11: A method for manipulating a surgical tool, said method comprising: providing a gripper mechanism attached to an arm of a surgical robot;
placing an elongate surgical tool between a pair of opposed bodies carried by the gripper mechanism; and
rotating the opposed bodies to frictionally engage the elongate tool, wherein the amount of friction is controlled by the degree of rotation of the opposed bodies.

Clause 12: The method of Clause 11, wherein rotating the opposed bodies comprises counterrotating the opposed bodies.

Clause 13: The method of Clause 11, wherein each opposed body has a cylindrical peripheral surface with a circumferentially oriented tapered groove formed therein, said grooves forming a circular aperture therebetween wherein (1) a diameter of the circular aperture varies as the opposed bodies are rotated and (2) a center of the circular aperture remains fixed relative to the gripper mechanism regardless of the rotational positions of the opposed bodies.

Clause 14: The method of Clause 13, wherein the cylindrical peripheral surface consists essentially of a partial cylindrical surface.

Clause 15: The method of Clause 13, wherein the opposed bodies are rotated to adjust the diameter of the circular aperture in the gripper mechanism to match a circumference of the elongate tool being held by the gripper mechanism.

Clause 16: The method of Clause 15, wherein the opposed bodies are further rotated to adjust a holding friction between the opposed bodies and the elongate tool.

Clause 17: The method of Clause 16, wherein the friction is adjusted to allow the elongate tool to be rotated, advanced, and/or retracted relative to the gripper while still being held by the gripper.

Clause 18: The method of Clause 17, further comprising at least one of manually rotating and manually translating the elongate tool in an axial direction while said elongate tool is being held by the gripper.

Clause 19: The method of Clause 11, wherein the elongate tool has a circular periphery where held by the gripping mechanism.

Clause 20: The method of Clause 11, wherein the elongate tool has a non-circular periphery where held by the gripper mechanism but is still circumferentially centered in the gripper mechanism.

Clause 21: The method of Clause 11, further comprising selectively attaching and detaching the gripper mechanism to a motor.

Clause 22: The method of Clause 11, further comprising performing a surgical procedure with the tool while held by the gripper mechanism.

Clause 23: The method of Clause 22, wherein the gripper mechanism is positioned in a non-sterile field during the surgical procedure.

Clause 24: The method of Clause 22, further comprising sterilizing the gripper mechanism after performing the surgical procedure.

Clause 25: The method of Clause 11, further comprising opening a pair of jaws on the gripper to create a space between said jaws, wherein each jaw carries one of the pair of opposed bodies and closing the jaws to capture the elongate tool.

Clause 26: A gripper for holding tools comprising:
a compartment housing a motor;
a shaft with a proximal end and a distal end, mechanically connected at its proximal end to the compartment;
a gripper mechanism comprising two opposing gripper elements, mechanically connected to the distal end of the shaft; and
at least two pairs of concentric shutter elements integral with the gripper mechanism configured to rotate selectively inward or outward to vary the circumference of an opening in the gripper mechanism;
wherein the shaft is configured to transfer motion from the motor to the gripper mechanism and the concentric shutter elements.

Clause 27: The gripper for holding tools of Clause 26, wherein the shaft is configured to transfer horizontal motion generated by the motor along the length of the shaft from its proximal end to its distal end in order to selectively open and close the gripper elements.

Clause 28: The gripper for holding tools of Clause 26, wherein the shaft is configured to transfer rotational motion generated by the motor to engage and selectively rotate inward or outward the concentric shutter elements.

Clause 29: The gripper for holding tools of Clause 26, wherein the shaft is configured to transfer horizontal motion generated by the motor along the length of the shaft from its proximal end to its distal end in order to selectively open and close the gripper elements and wherein the shaft is further configured to transfer rotational motion generated by the motor to engage and selectively rotate inward or outward the concentric shutter elements.

Clause 30: The gripper for holding tools of Clause 29, further comprising a vertical shaft housing gears engaged to the concentric shutter elements, wherein the rotational motion causes rotation of the gears that, in turn, causes the concentric shutter elements to selectively rotate inward or outward.

Clause 31: The gripper for holding tools of Clause 26, wherein the circumference of the opening in the gripper mechanism is varied to match the circumference of a tool being held by the gripper mechanism.

Clause 32: The gripper for holding tools of Clause 31, wherein the tool is circumferentially centered in the gripper mechanism.

Clause 33: The gripper for holding tools of Clause 32, wherein the tool has a non-constant circumferential radius but is still circumferentially centered in the gripper mechanism.

Clause 34: The gripper for holding tools of Clause 26, wherein the shaft is selectively detachable from the compartment housing the motor.

Clause 35: The gripper for holding tools of Clause 26, wherein the tool can be rotated while being held by the gripper mechanism.

Clause 36: The gripper for holding tools of Clause 26, wherein the gripper for holding tools is an end effector of a robotic system.

Clause 37: The gripper for holding tools of Clause 36, wherein the robotic system is a surgical robotic system.

Clause 38: The gripper for holding tools of Clause 37, wherein the compartment housing therefor is configured to be positioned in the non-sterile field during a surgical procedure.

Clause 39: The gripper for holding tools of Clause 37, wherein the shaft and gripper mechanism are configured to be positioned in the sterile field during a surgical procedure.

Clause 40: The gripper for holding tools of Clause 39, wherein the shaft and gripper mechanism are configured to be sterilizable after being detached from the compartment housing the motor.

Clause 41: A gripper assembly for holding tools, said gripper assembly comprising:
 a housing configured for mounting on a robotic arm;
 a gripper mechanism coupled to the housing and comprising at least one pair of opposed bodies each having a cylindrical peripheral surface;
 wherein the cylindrical peripheral surfaces are configured to define opposed arcuate gripping surface which define a generally circular periphery with (1) a diameter that depends on the rotational positions of the opposed bodies and (2) a center that remains fixed relative to the gripper mechanism regardless of the rotational positions of the opposed bodies.

Clause 42: The gripper assembly of Clause 41, wherein the cylindrical peripheral surfaces have circumferentially oriented tapered grooves formed therein, the tapered grooves are shaped similarly and have radii that decrease from an initial end of the groove to a terminal end of the groove and wherein the opposed bodies are configured to rotate about their respective axes to orient the tapered grooves to form the generally circular periphery.

Clause 43: The gripper assembly of Clause 42, further comprising a shaft having a distal end connected to the gripper mechanism and a proximal end configured to be connected to a motor which can rotate the shaft to counter-rotate the opposed bodies.

Clause 44: The gripper assembly of Clause 43, further comprising a gear chain configured to transfer rotation from the shaft to the opposed bodies.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A gripper assembly for holding tools, said gripper assembly comprising: a housing configured for mounting on a robotic arm;
 a gripper mechanism coupled to the housing and comprising at least one pair of opposed bodies each having a cylindrical peripheral surface with a circumferentially oriented tapered groove formed therein;
 wherein the tapered grooves are shaped similarly and have partial circular cross-sections with radii that decrease from an initial end of the groove to a terminal end of the groove and wherein the opposed bodies are configured to rotate about their respective axes to orient the tapered grooves to form a gripping surface with a generally continuous circular periphery with (1) a diameter that depends on the rotational positions of the opposed bodies and (2) a center that remains fixed relative to the gripper mechanism regardless of the rotational positions of the opposed bodies.

2. The gripper assembly of claim 1, wherein the opposed bodies are configured to counterrotate.

3. The gripper assembly of claim 1, further comprising a shaft having a distal end connected to the gripper mechanism and a proximal end configured to be connected to a motor which can rotate the shaft to counterrotate the opposed bodies.

4. The gripper assembly of claim 3, further comprising a gear chain configured to transfer rotation from the shaft to the opposed bodies.

5. The gripper assembly of claim 4, wherein the gear chain includes a vertical shaft having a worm gear which drives gear wheels connected to each of the opposed bodies.

6. The gripper assembly of claim 3, wherein the gripper mechanism further comprises a pair of jaws pivotally attached to the housing.

7. The gripper assembly of claim 6, wherein each jaw carries one of the opposed bodies of each pair.

8. The gripper assembly of claim 7, wherein the jaws are configured to move the tapered grooves on the opposed bodies into and out of proximity to facilitate positioning tools therebetween.

9. The gripper assembly of claim 8, further comprising a lever assembly coupled to the shaft and configured to transfer axial translation of the shaft to open and close the jaws.

10. The gripper assembly of claim 1, wherein the opposed bodies are configured to control an amount of friction applied to a tool held by the opposed bodies in response to a degree of rotation of the opposed bodies.

11. A method for manipulating a surgical tool, said method comprising:
providing a gripper mechanism attached to an arm of a surgical robot, said gripper mechanism comprising opposed bodies which are configured to rotate about their respective axes, wherein said respective axes are parallel to and spaced apart from each other;
placing an elongate surgical tool between the pair of opposed bodies carried by the gripper mechanism in a direction perpendicular to the respective axes of the opposed bodies; and
rotating the opposed bodies about their respective axes to frictionally engage the elongate tool, wherein the amount of friction is controlled by the degree of rotation of the opposed bodies.

12. The method of claim 11, wherein rotating the opposed bodies comprises counterrotating the opposed bodies.

13. The method of claim 11, wherein each opposed body has a cylindrical peripheral surface with a circumferentially oriented tapered groove formed therein, said grooves forming a circular aperture therebetween wherein (1) a diameter of the circular aperture varies as the opposed bodies are rotated and (2) a center of the circular aperture remains fixed relative to the gripper mechanism regardless of the rotational positions of the opposed bodies.

14. The method of claim 13, wherein the cylindrical peripheral surface consists essentially of a partial cylindrical surface.

15. The method of claim 13, wherein the opposed bodies are rotated to adjust the diameter of the circular aperture in the gripper mechanism to match a circumference of the elongate tool being held by the gripper mechanism.

16. The method of claim 15, wherein the opposed bodies are further rotated to adjust a holding friction between the opposed bodies and the elongate tool.

17. The method of claim 16, wherein the friction is adjusted to allow the elongate tool to be rotated, advanced, and/or retracted relative to the gripper while still being held by the gripper.

18. The method of claim 17, further comprising at least one of manually rotating and manually translating the elongate tool in an axial direction while said elongate tool is being held by the gripper.

19. The method of claim 11, wherein the elongate tool has a circular periphery where held by the gripping mechanism.

20. The method of claim 11, wherein the elongate tool has a non-circular periphery where held by the gripper mechanism but is still circumferentially centered in the gripper mechanism.

21. The method of claim 11, further comprising selectively attaching and detaching the gripper mechanism to a motor.

22. The method of claim 11, further comprising performing a surgical procedure with the tool while held by the gripper mechanism.

23. The method of claim 22, wherein the gripper mechanism is positioned in a non-sterile field during the surgical procedure.

24. The method of claim 22, further comprising sterilizing the gripper mechanism after performing the surgical procedure.

25. The method of claim 11, further comprising opening a pair of jaws on the gripper to create a space between said jaws, wherein each jaw carries one of the pair of opposed bodies and closing the jaws to capture the elongate tool.

26. A gripper for holding tools comprising:
a compartment housing a motor;
a shaft with a proximal end and a distal end, mechanically connected at its proximal end to the compartment;
a gripper mechanism comprising two opposing gripper elements, pivotally connected to the distal end of the shaft, said opposing gripper elements having a tool-receiving passage therebetween; and
at least two pairs of concentric shutter elements integral with the gripper mechanism configured to rotate selectively inward or outward to vary a diameter of a circular opening in the in the tool-receiving passage of the gripper mechanism;
wherein one shutter element from each of said at least two pairs of shutter elements is mounted on each of the two opposing gripper elements; and
wherein the shaft is configured to transfer motion from the motor to the gripper mechanism and the concentric shutter elements.

27. A gripper assembly for holding tools, said gripper assembly comprising:
a housing configured for mounting on a robotic arm;
a gripper mechanism coupled to the housing and comprising at least one pair of opposed bodies each having a cylindrical peripheral surface;
wherein the cylindrical peripheral surfaces are configured to define opposed arcuate gripping surface which define a generally circular periphery with (1) a diameter that depends on the rotational positions of the opposed bodies and (2) a center that remains fixed relative to the gripper mechanism regardless of the rotational positions of the opposed bodies.

28. The gripper assembly of claim 27, wherein the cylindrical peripheral surfaces have circumferentially oriented tapered grooves formed therein, the tapered grooves are shaped similarly and have radii that decrease from an initial end of the groove to a terminal end of the groove and wherein the opposed bodies are configured to rotate about their respective axes to orient the tapered grooves to form the generally circular periphery.

29. The gripper assembly of claim 28, further comprising a shaft having a distal end connected to the gripper mechanism and a proximal end configured to be connected to a motor which can rotate the shaft to counterrotate the opposed bodies.

30. The gripper assembly of claim 29, further comprising a gear chain configured to transfer rotation from the shaft to the opposed bodies.

* * * * *